(12) United States Patent
Duez et al.

(10) Patent No.: US 9,783,569 B2
(45) Date of Patent: Oct. 10, 2017

(54) METHOD FOR PREPARING 6-ALKYLATED STEROIDAL DERIVATIVES AND CORRESPONDING ALKYLATED 5,6,7,8-TETRAHYDRONAPHTHALENE-2(4 ALPHA.H)-ONES

(71) Applicant: SANOFI, Paris (FR)

(72) Inventors: Stéphanie Duez, Munich (DE); Jean-Luc Haesslein, Paris (FR); Frédéric Lhermitte, Paris (FR); Pauline Quinio, Munich (DE)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 15/032,251

(22) PCT Filed: Oct. 28, 2014

(86) PCT No.: PCT/FR2014/052740
§ 371 (c)(1),
(2) Date: Apr. 26, 2016

(87) PCT Pub. No.: WO2015/063408
PCT Pub. Date: May 7, 2015

(65) Prior Publication Data
US 2016/0244478 A1    Aug. 25, 2016

(30) Foreign Application Priority Data
Oct. 28, 2013   (FR) ..................................... 13 60498

(51) Int. Cl.
*C07J 9/00* (2006.01)
*C07J 21/00* (2006.01)
*C07C 45/68* (2006.01)
*C07J 5/00* (2006.01)

(52) U.S. Cl.
CPC ............ *C07J 21/008* (2013.01); *C07C 45/68* (2013.01); *C07J 5/0076* (2013.01); *C07J 9/005* (2013.01); *C07C 2602/28* (2017.05); *C07J 21/00* (2013.01)

(58) Field of Classification Search
CPC ............ C07J 9/00; C07J 21/00; C07C 45/68
USPC .... 540/12, 14; 552/580, 590, 596, 597, 598, 552/605, 611
See application file for complete search history.

(56) References Cited

U.S. PATENT DOCUMENTS

| | | | |
|---|---|---|---|
| 2,816,902 | A | 12/1957 | Gould et al. |
| 2,908,696 | A | 10/1959 | Nussbaum et al. |
| 2,959,602 | A | 11/1960 | Gould et al. |
| 4,322,349 | A | 3/1982 | Annen et al. |

FOREIGN PATENT DOCUMENTS

| | | |
|---|---|---|
| DE | 1059906 B | 6/1959 |
| EP | 0034115 A2 | 8/1981 |
| FR | 1 590 064 A | 4/1970 |
| GB | 926472 A | 5/1963 |
| GB | 1051613 A | 12/1966 |
| IL | 59161 A | 11/1983 |
| WO | WO-93/00354 A1 | 1/1993 |

OTHER PUBLICATIONS

Annen, K. et al. (1982). "A Simple Method for 6-Methylation of 3-Oxo-Δ4-steroids" *Synthesis* pp. 34-40.
Annen, K. et al. (1983). "17-Pivalate in Der Pregnanreihe//17-Pivalate Derivatives of Pregnane," Liebigs Annalen Der Chemie, Verlag Chemie GmbH, Weinheim, Germany 4: 705-711.
Burn, D. et al. (Oct. 17, 1968). "Modified Steroid Hormones—LI, Application of the Vilsmeier Reaction to 11β-Hydroxy Steroids," *Tetrahedron* 25:1155-1158.
Fried, J.H. et al. (Mar. 5, 1959). "Alkylated Adrenal Hormones. The Synthesis of 6α-Methyl Cortical Steroids," *J. Am. Chem. Soc.* 81(5):1235-1239.
International Search Report and Written Opinion mailed Jul. 28, 2015, for PCT Application No. PCT/FR2014/052740 filed on Oct. 28, 2014, 33 pages.
Lal, G.S. (1993). "Site-selective Fluorination of Organic Compounds Using 1-alkyl-4-flouro-1, 4-diazabicyclo [2.2.2]octane Salts (Selectfluor Reagents)," *J. Org. Chem.* 58(10):2791-2796.
Li et al. (2010) "Synthesis of 11, 17, 21-triacetoxy-6α-fluoro-pregn-1,4-diene-3,20-dione," Huaxue Yu Shengwu Gongcheng, 27(8), 42-43, 47 CODEN: HYSGAF; ISSN:1672-5425, one page.
Paquette, L.A. et al. (Jul. 12, 2002). "Applications of the Squarate Ester Cascade to the Expeditious Synthesis of Hypnophilin, Coriolin, and Ceratopicanol," *J. Am. Chem. Soc.* 124(31):9199-9203.
Ringold, H.J. et al. (Jul. 5, 1959). "Steroids. CXXVII.1 6—Halo Progestational Agents," *J. Am. Chem. Soc.* 81(13):3485-3486.
Volkers, A.A. et al. (2009, e-pub: Oct. 17, 2008) "Alkylations of Tricyclo [5.2.1.02,6] deca-4,8-dien-3-one by a cuprate reaction," *Tetrahedron* 65(1):389-395.

*Primary Examiner* — Brenda Coleman

(74) *Attorney, Agent, or Firm* — Morrison & Foerster LLP

(57) ABSTRACT

The present invention concerns a method for preparing certain steroidal derivatives alkylated in position 6, comprising a step of alkylating the corresponding compound halogenated in position 6 with an organometallic alkylating agent.

27 Claims, No Drawings

METHOD FOR PREPARING 6-ALKYLATED STEROIDAL DERIVATIVES AND CORRESPONDING ALKYLATED 5,6,7,8-TETRAHYDRONAPHTHALENE-2(4 ALPHA.H)-ONES

CROSS REFERENCE TO RELATED APPLICATIONS

This application is a National Phase application under 35 U.S.C. §371 of International Application No. PCT/FR2014/052740 filed Oct. 28, 2014, which claims priority benefit to FR Application No. 1360498 filed Oct. 28, 2013, the disclosures of each of which are herein incorporated by reference in their entirety.

A subject matter of the present invention is a process for the alkylation of compounds of formula (III):

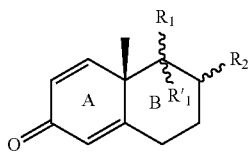

(III)

to give compounds of formula (I):

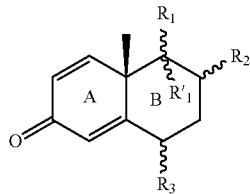

(I)

where $R_1$ and $R_2$ represent, independently of one another, a hydrogen atom, an alkyl radical comprising from 1 to 3 carbon atoms or a halogen atom, or else $R_1$ and $R_2$ together form a carbon-based ring comprising from 4 to 6 carbon atoms which is ortho-fused to the B ring of the compound (I), said ring optionally comprising one or more double bonds and being optionally substituted by one or more alkyl groups comprising from 1 to 3 carbon atoms, or else $R_1$ and $R_2$ together form the C and D rings of a steroidal carbon-based backbone, said rings C and D optionally comprising one or more double bonds and being optionally substituted by one or more groups chosen from linear or branched alkyl groups comprising from 1 to 12 carbon atoms, acyl groups comprising from 1 to 12 carbon atoms and optionally substituted by one or more hydroxyl groups, carboxyl, hydroxyl or oxo groups, in the free or protected form, or halogen atoms, preferably fluorine, it being possible for each position of said C and D rings to carry one or, when this is possible, two substituents, $R'_1$ represents a hydrogen or halogen atom, preferably fluorine, and $R_1$ and $R'_1$ are located on either side of the plane of the A and B rings, $R_3$ represents an alkyl group comprising from 1 to 4 carbon atoms, preferably a methyl group, preferably a methyl group positioned in the α position, ═ represents a single bond or a double bond, and ∼∼∼ represents either a single bond in the α or β position of the A and B rings or a double bond in the plane of the A and B rings.

In particular, a subject matter of the present invention is a process for the preparation of 6-alkyl-3-oxo-$\Delta^{1,4}$-pregnadienes or 6-alkyl-3-oxo-4-pregnenes, of formula (IA) below:

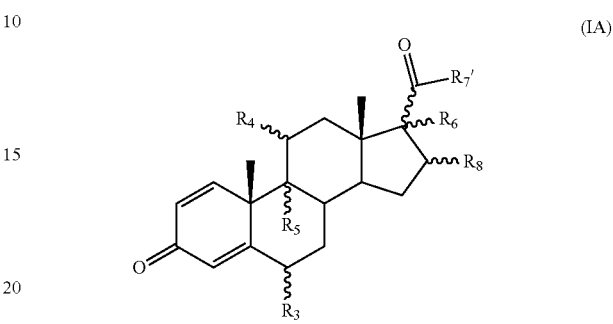

(IA)

where $R_3$ is an alkyl group comprising from 1 to 4 carbon atoms, preferably a methyl, $R_4$ is either hydrogen or a hydroxyl or oxo group, in the free or protected form, for example a hydroxyl group in the esterified form, preferably in the acetylated form or in the trifluoroacetylated form, $R_5$ is either a hydrogen atom or a halogen atom, preferably fluorine, $R_6$ is either a hydrogen atom or a hydroxyl group, in the free or protected form, for example in the esterified form, $R_7'$ is either hydrogen, or an alkyl group comprising from 1 to 3 carbon atoms, or a hydroxyl group, in the free or protected form, or a hydroxyalkyl group comprising from 1 to 3 carbon atoms, in the free or protected form, preferably a hydroxymethyl group, in the free or protected form, preferably a hydroxymethyl group in the acetylated form or in the trifluoroacetylated form, $R_8$ is either a hydrogen atom or an alkyl group comprising from 1 to 3 carbon atoms, where the —$R_6$ and —(CO)$R_7'$ groups are located on either side of the plane of the A, B, C and D rings, where the oxo group located on the carbon in the 20 position of the steroidal backbone can be in the free or protected form, where ═ represents a single bond or a double bond, where ∼∼∼ represents either a single bond in the α or β position or in the plane of the A, B, C and D rings or, when this is possible, a double bond in the plane of the A, B, C and D rings.

In the case of the steroids, the introduction into the 6 position of an alkyl substituent, in particular a methyl substituent, has the effect of increasing the activity or of reducing the undesirable effects, in comparison with the corresponding non-alkylated structure. This is the case, for example, for progestogen agents, such as megestrol or megestrol acetate, medrogestone, medroxyprogesterone or medroxyprogesterone acetate, and corticosteroids, such as 6-α-methylprednisolone, medrysone, endrysone, fluorometholone or cortivazol, which are steroids methylated in the 6 position.

The processes of the prior art for the alkylation of steroidal compounds in the 6 position have it in common that the alkylation is carried out on a structure saturated in the 1,2 position.

In particular, the known methylation processes involve the introduction of a methylene at the 6 position on a structure saturated in the 1,2 position.

The methylene can subsequently be converted into α- or β-methyl by hydrogenation, according to the method described in the publication "Modified Steroid Hormones, Application of the Vilsmeier Reaction to 11β-Hydroxysteroids", D Burn and J. P. Yardley, Tetrahedron, Vol. 25, pp 1155-1158.

An optional stage of creating the double bond at the 1,2 position is carried out, subsequent to the alkylation, with dehydrogenating agents, such as 2,3-dichloro-5,6 dicyano-1,4-benzoquinone, as described in the patent GB 1 051 613, or else with other known chemical or microbiological methods, for example described in the application IL59161.

The introduction of the methylene onto the structure saturated in the 1,2 position can be carried out as described in the patent EP 0 034 115 or in the publication "A Simple Method for 6-Methylation of 3-oxo-$\Delta^4$-steroids", Annen et al., Synthesis, January 1982, 34-40, by reaction with a formaldehyde acetal in the presence of phosphoric acid derivatives.

This introduction of the methylene can also be carried out, as described in the application WO93/00354, by a Mannich reaction using formaldehyde and a secondary amine (N-methylaniline), catalyzed by trifluoroacetic acid in tetrahydrofuran.

However, these methods comprise a large number of stages.

Furthermore, in the case of the synthesis of compounds which are unsaturated in the 1,2 position of the ring corresponding to the A ring of a steroidal backbone, it can be advantageous to carry out the direct alkylation of a structure already possessing this unsaturation, for example, for steroids, the direct alkylation of a $\Delta^{1,4}$-pregnadiene structure. This is, for example, advantageous for the synthesis of 6α-methylprednisolone, endrysone or fluorometholone.

There thus exists a need for the development of simple and economical routes for the introduction of an alkyl substituent, in particular a methyl substituent, at the 6 position of these structures.

A subject matter of the present invention is such alkylation processes. This is because a subject matter of the present invention is processes for the preparation of compounds corresponding to the formula (I) below:

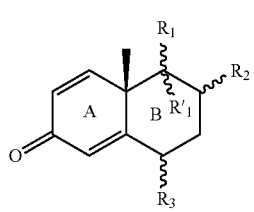

(I)

where $R_1$ and $R_2$ represent, independently of one another, a hydrogen atom, an alkyl radical comprising from 1 to 3 carbon atoms or a halogen atom, or else $R_1$ and $R_2$ together form a carbon-based ring comprising from 4 to 6 carbon atoms which is ortho-fused to the B ring of the compound (I), said ring optionally comprising one or more double bonds and being optionally substituted by one or more alkyl groups comprising from 1 to 3 carbon atoms, or else $R_1$ and $R_2$ together form the C and D rings of a steroidal carbon-based backbone, said rings C and D optionally comprising one or more double bonds and being optionally substituted by one or more groups chosen from linear or branched alkyl groups comprising from 1 to 12 carbon atoms, acyl groups comprising from 1 to 12 carbon atoms and optionally substituted by one or more hydroxyl groups, carboxyl, hydroxyl or oxo groups, in the free or protected form, or halogen atoms, preferably fluorine, it being possible for each position of said C and D rings to carry one or, when this is possible, two substituents, $R'_1$ represents a hydrogen or halogen atom, preferably fluorine, and $R_1$ and $R'_1$ are located on either side of the plane of the A and B rings, $R_3$ represents an alkyl group comprising from 1 to 4 carbon atoms, preferably a methyl group, preferably a methyl group positioned in the α position, ═ represents a single bond or a double bond, and ⁓⁓⁓ represents either a single bond in the α or β position of the A and B rings or a double bond in the plane of the A and B rings.

The processes according to the invention comprise a stage of alkylation of a compound of formula (II):

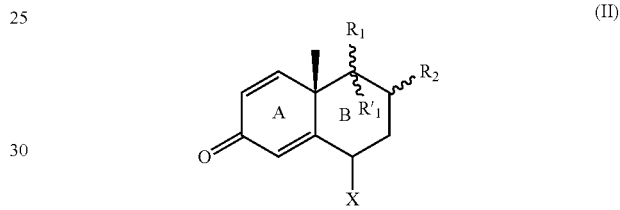

(II)

where $R_1$, $R'_1$ and $R_2$, ═ and ⁓⁓⁓ are as defined in the compound (I), where X is a halogen atom, preferably bromine or iodine, preferably bromine, with an organometallic alkylating agent, which makes it possible to introduce an alkyl group $R_3$ as replacement for the halogen atom X of the compound (II), optionally in the presence of a metal catalyst, preferably a palladium or copper catalyst, in order to result in the compound of formula (I).

The compound (II) can be obtained by halogenation, according to techniques known to a person skilled in the art, of a compound of formula (III):

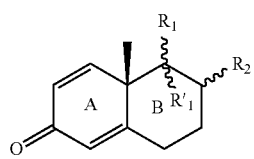

(III)

where $R_1$, $R'_1$ and $R_2$, ═ and ⁓⁓⁓ are as defined above.

For example, a bromination of the compound (III) can be carried out by reaction with an N-bromoimide, such as N-bromosuccinimide, in the presence of a radical initiator, such as benzoyl peroxide or AIBN (azobisisobutyronitrile), according to the conventional conditions of a Wohl-Ziegler reaction.

Protection of the hydroxyl group is understood to mean any normal protection known to a chemist. Mention may be made, for example, of cleavable ethers, such as those formed with a $C_{(1-6)}$ alkyl group, in particular a methyl or t-butyl group, with a $C_{(1-6)}$ alkylphenyl group, in particular a benzyl, p-methoxybenzyl or p-nitrobenzyl group, allyl, trityl, methoxymethyl, methoxyethoxymethyl, ethoxyethyl or tetrahydropyranyl ethers, or silylated ethers, in particular trimethylsilyl, triethylsilyl or triisopropylsilyl, t-butyldimethylsilyl or dimethylarylsilyl ethers.

Mention may also be made of cleavable esters, such as, for example, those formed with an acetyl, benzoyl, phenylacetyl, formyl or haloacetyl group, such as a chloroacetyl, dichloroacetyl or trichloroacetyl group, or a trifluoroacetyl group. Mention may also be made of carbonates, and also cyclic ketals, such as —O—(CH$_2$)$_m$—O—, m preferably being 1, 2 or 3.

Protection of the oxo group is understood to mean any protection known to a chemist and in particular acetals, cyclic ketals and thioketals, such as —O—(CH$_2$)$_m$—O—, —O—(CH$_2$)$_m$—S—, —S—(CH$_2$)$_m$—S— or —O—CH$_2$—C(C$_{1-4}$ alkyl)$_2$-CH$_2$—O—, or acyclic ketals, such as (CH$_3$O)$_2$— or (EtO)$_2$—, m preferably being 1, 2 or 3.

When the compounds (I), (II) and (III) of the processes according to the invention comprise adjacent oxo and/or hydroxyl groups, these can be protected jointly by one and the same acetal, cyclic ketal or cyclic thioketal, such as those mentioned above.

The protection of adjacent oxo and/or hydroxyl groups by cyclic ketals can also result in the formation of oxaspirane compounds.

For example, in an alternative form of the processes according to the invention, it is noted that the specific compounds (Id) and (IId) below, where X represents a halogen atom, preferably bromine or iodine, preferably bromine, can occur in the free form:

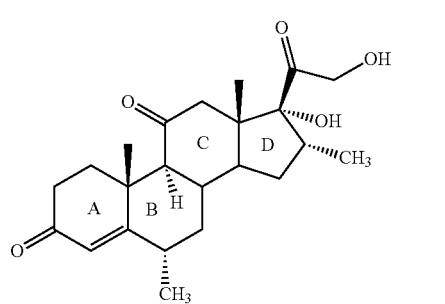
(Id)

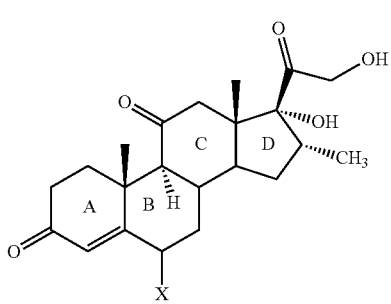
(IId)

or can comprise protection in the form of an oxaspirane group (here 2,4,7,9-oxaspiro[4.5]nonane group).

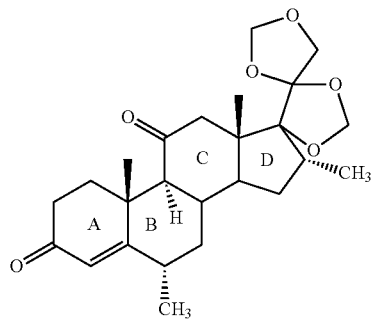
(Id')

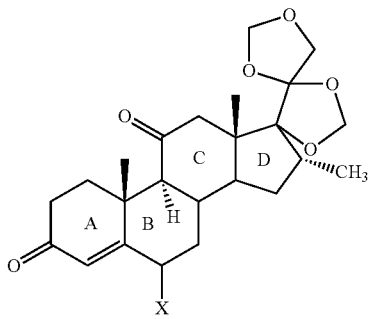
(IId')

In this example, the free form is converted to the protected form by a treatment with formaldehyde in the presence of an acid, according to known techniques.

The compounds (Id), (IId), (Id') and (IId') described above are intermediates of use in the synthesis of cortivazol, a corticosteroid known for its anti-inflammatory and immunosuppressant effect. The synthesis of cortivazol from compounds in the free form respectively of formulae (Id) and (IId) or in the protected form respectively of formula (Id) or (IId') is, for example, described in the patent FR 1 590 064.

Another subject matter of the present invention is said intermediates of formula (IId) or (IId').

Protection of the carboxyl group is understood to mean esterified carboxyl group, in particular a C$_{(1-6)}$ alkyl, benzyl or allyl ester, or a silyl ester, for example triethylsilyl or trimethylsilyl ester.

In the processes according to the invention, the stage of alkylation of the halogenated compound (II) can be carried out in any appropriate solvent, for example tetrahydrofuran, 2-methyltetrahydrofuran, ethyl ether or dioxane, preferably at a temperature of between −70 and 0° C. (−40° C. in the examples).

The alkylating agents can optionally be prepared in situ. For example, in the case of organocuprates, it is possible to react the corresponding organolithium compound with copper iodide.

An important advantage of the alkylating processes according to the invention is that they do not require the addition of an excess of copper. This is because complete alkylation is obtained from one equivalent of copper, with respect to the compound (II) to be alkylated. Thus, the processes according to the invention operate with a reduced content of metal.

Typically, the amount of copper introduced is between 1 and 2 equivalents, with respect to the compound (II) to be alkylated, preferably between 1 and 1.5 equivalents, preferably between 1.1 and 1.3 equivalents, typically 1.2 equivalents.

A subject matter of the present invention is thus a process for the preparation of a compound of formula (I):

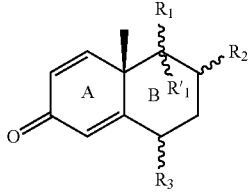

(I)

where R₁ and R₂ represent, independently of one another, a hydrogen atom, an alkyl radical comprising from 1 to 3 carbon atoms or a halogen atom, or else R₁ and R₂ together form a carbon-based ring comprising from 4 to 6 carbon atoms which is ortho-fused to the B ring of the compound (I), said ring optionally comprising one or more double bonds and being optionally substituted by one or more alkyl groups comprising from 1 to 3 carbon atoms, or else R₁ and R₂ together form the C and D rings of a steroidal carbon-based backbone, said rings C and D optionally comprising one or more double bonds and being optionally substituted by one or more groups chosen from linear or branched alkyl groups comprising from 1 to 12 carbon atoms, acyl groups comprising from 1 to 12 carbon atoms and optionally substituted by one or more hydroxyl groups, carboxyl, hydroxyl or oxo groups, in the free or protected form, or halogen atoms, preferably fluorine, it being possible for each position of said C and D rings to carry one or, when this is possible, two substituents, R'₁ represents a hydrogen or halogen atom, preferably fluorine, and R₁ and R'₁ are located on either side of the plane of the A and B rings, R₃ represents an alkyl group comprising from 1 to 4 carbon atoms, preferably a methyl group, preferably a methyl group positioned in the α position, ═ represents a single bond or a double bond, and ⁓⁓⁓ represents either a single bond in the α or β position of the A and B rings or a double bond in the plane of the A and B rings, comprising a stage of alkylation of a compound of formula (II):

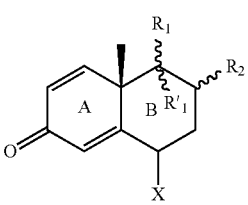

(II)

where R₁, R'₁ and R₂, ═ and ⁓⁓⁓ are as defined in the compound (I), where X is a halogen atom, preferably bromine or iodine, preferably bromine, with an organometallic alkylating agent, which makes it possible to introduce an alkyl group R₃ as replacement for the halogen atom X of the compound (II), optionally in the presence of a metal catalyst, preferably a palladium or copper catalyst, in order to result in the compound of formula (I).

According to one embodiment, the alkylating agent is chosen from organolithium compounds of formula R₃Li, organomagnesium compounds of formula R₃MgX', organozinc compounds of formula R₃ZnX', where X' is a halogen atom, preferably chlorine or bromine, organocopper compounds of formula R₃Cu, lithium organocuprates of formula (R₃)₂CuLi or organocyanocuprates of formula R₃CuCNLi or (R₃)₂CuCN(Li)₂, halocuprates of formula R₃CuLiX'', where X'' is a halogen, preferably iodine or bromine, organoboron compounds of formula R₃B(OH)₂ or organotrifluoroborates of formula R₃BF₃K, optionally in the presence of a metal catalyst, preferably a nickel, palladium or copper catalyst, preferably a palladium or copper catalyst.

According to a specific embodiment, the alkylating agent is chosen from organomagnesium compounds, organocopper compounds, lithium organocuprates, organocyanocuprates or halocuprates.

According to another embodiment, the alkylating agent is an organomagnesium compound of formula R₃MgX', where X' is a halogen atom, preferably chlorine or bromine, preferably bromine, and where the alkylation is carried out in the presence of a copper catalyst.

Another subject matter of the present invention is such a process where the alkylating agent is a halocuprate of formula R₃CuLiX'', where X'' is a halogen, preferably iodine or bromine.

Another subject matter of the present invention is such a process where the alkylating agent is a lithium organocuprate of formula (R₃)₂CuLi or an organocyanocuprate of formula (R₃)₂CuCN(Li)₂.

Another subject matter of the present invention is such a process where the alkylating agent is a lithium organocuprate of formula (R₃)₂CuLi and where the alkylation comprises a stage of reaction of the compound (II) with said lithium organocuprate, followed by a reaction of the compound thus obtained with a second alkylating agent of formula R₃X''', where X''' is a halogen atom, preferably iodine.

According to one embodiment of the processes according to the invention, the compound (II) is obtained by halogenation of a compound of formula (III):

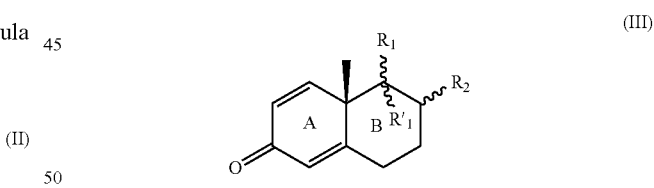

(III)

where R₁, R'₁, R₂, ═ and ⁓⁓⁓ are as defined above.

According to one embodiment of the processes according to the invention, X represents a bromine atom.

According to one embodiment of the processes according to the invention, the compound (II) is obtained by reaction of the compound (III) with an N-bromoimide, such as N-bromosuccinimide, in the presence of a radical initiator, such as benzoyl peroxide or azobisisobutyronitrile.

According to one embodiment of the processes according to the invention, in the compounds of formulae (I) and (II), R₁ and R₂ together form the C and D rings of a steroidal carbon-based backbone, said rings C and D optionally comprising one or more double bonds and being optionally substituted by one or more groups chosen from linear or branched alkyl groups comprising from 1 to 12 carbon atoms, acyl groups comprising from 1 to 12 carbon atoms and optionally substituted by one or more hydroxyl groups, carboxyl, hydroxyl or oxo groups, in the free or protected form, or halogen atoms, preferably fluorine, it being possible for each position of said C and D rings to carry one or, when this is possible, two substituents.

According to one embodiment of the processes according to the invention, the compound (I) is a steroidal compound of formula (IA):

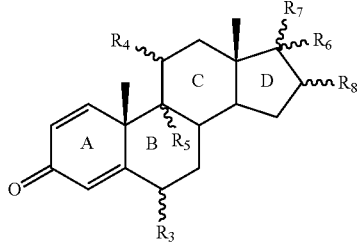

(IA)

where $R_3$ is an alkyl group comprising from 1 to 4 carbon atoms, preferably a methyl,
$R_4$ is either hydrogen or a hydroxyl or oxo group, in the free or protected form, for example a hydroxyl group in the esterified form, preferably in the acetylated form or in the trifluoroacetylated form,
$R_5$ is either hydrogen or a halogen atom, preferably fluorine,
$R_6$ is either hydrogen or a hydroxyl group, in the free or protected form,
$R_7$ is either hydrogen or a —C(O)$R_7$' or —C(OR)$_2$$R_7$' group, where R is a protective group for the carbonyl functional group and where $R_7$' is either hydrogen, or an alkyl group comprising from 1 to 3 carbon atoms, or a hydroxyl group, in the free or protected form, or a hydroxyalkyl group comprising from 1 to 3 carbon atoms, in the free or protected form, preferably a hydroxymethyl group, in the free or protected form, preferably a hydroxymethyl group in the acetylated form or in the trifluoroacetylated form, or else $R_6$ and $R_7$ together form an oxo group in the 17 position of the steroidal backbone of the compound (IA),
$R_8$ is either hydrogen or an alkyl group comprising from 1 to 3 carbon atoms,
where the —$R_6$ and —$R_7$ groups are located on either side of the plane of the A, B, C and D rings,
where ═ represents a single bond or a double bond,
where ⁓ represents either a single bond in the α or β position or in the plane of the A, B, C and D rings or, when this is possible, a double bond in the plane of the A, B, C and D rings, and the compound (II) is a compound of formula (IIA):

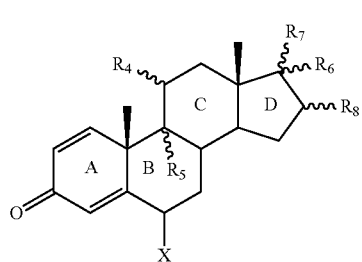

(IIA)

where $R_4$ and $R_5$, $R_6$, $R_7$, $R_8$, ═ and ⁓ are as defined in the compound (IA), where X is a halogen atom, preferably bromine or iodine, preferably bromine.

According to one embodiment of the processes according to the invention, the compound (I) is a steroidal compound of formula (IA):

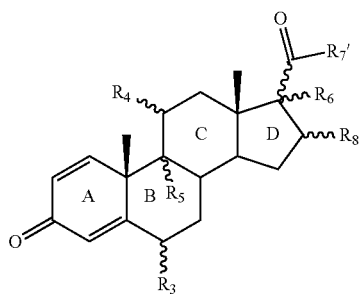

(IA)

where $R_3$ is an alkyl group comprising from 1 to 4 carbon atoms, preferably a methyl,
$R_4$ is either hydrogen or a hydroxyl or oxo group, in the free or protected form, for example a hydroxyl group in the esterified form, preferably in the acetylated form or in the trifluoroacetylated form,
$R_5$ is either hydrogen or a halogen atom, preferably fluorine,
$R_6$ is either hydrogen or a hydroxyl group, in the free or protected form,
$R_7$' is either hydrogen, or an alkyl group comprising from 1 to 3 carbon atoms, or a hydroxyl group, in the free or protected form, or a hydroxyalkyl group comprising from 1 to 3 carbon atoms, in the free or protected form, preferably a hydroxymethyl group, in the free or protected form, preferably a hydroxymethyl group in the acetylated form or in the trifluoroacetylated form,
$R_8$ is either hydrogen or an alkyl group comprising from 1 to 3 carbon atoms,
where the —$R_6$ and —(CO)$R_7$' groups are located on either side of the plane of the A, B, C and D rings,
where the oxo group located on the carbon in the 20 position of the steroidal backbone can be in the free or protected form,
where ═ represents a single bond or a double bond,
where ⁓ represents either a single bond in the α or β position or in the plane of the A, B, C and D rings or, when this is possible, a double bond in the plane of the A, B, C and D rings, and the compound (II) is a compound of formula (IIA):

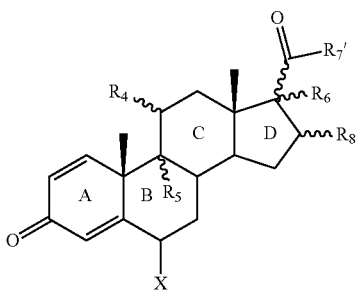

(IIA)

where $R_4$ and $R_5$, $R_6$, $R_7$', $R_8$, ═ and ⁓ are as defined in the compound (IA), where the oxo group located on the 20 carbon of the steroidal backbone can be in the free or protected form, where X is a halogen atom, preferably bromine or iodine, preferably bromine.

According to one embodiment of the processes according to the invention, the compound (I) is a compound of formula (IB):

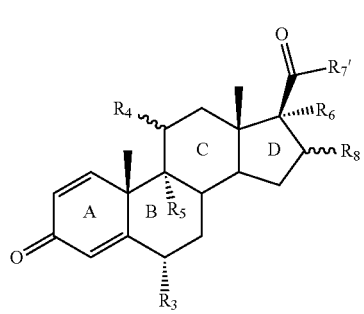

(IB)

where $R_3$ is an alkyl group comprising from 1 to 4 carbon atoms, preferably a methyl,
$R_4$ is either hydrogen, or a β-hydroxyl group, in the free or protected form, for example a hydroxyl group in the esterified form, preferably in the acetylated form or in the trifluoroacetylated form, or an oxo group, in the free or protected form,
$R_5$ is either hydrogen or a halogen atom, preferably fluorine,
$R_6$ is either hydrogen or a hydroxyl group, in the free or protected form, for example in the esterified form,
$R_7'$ is either hydrogen, or an alkyl group comprising from 1 to 3 carbon atoms, or a hydroxyl group, in the free or protected form, or a hydroxyalkyl group comprising from 1 to 3 carbon atoms, in the free or protected form, preferably a hydroxymethyl group, in the free or protected form, preferably a hydroxymethyl group in the acetylated form or in the trifluoroacetylated form,
$R_8$ is either hydrogen or an α-alkyl group comprising from 1 to 3 carbon atoms,
where the oxo group located on the 20 carbon of the steroidal backbone can be in the free or protected form,
where ═══ represents a single bond or a double bond,
where ⁓⁓⁓ represents either a single bond in the α or β position or in the plane of the A, B, C and D rings or, when this is possible, a double bond in the plane of the A, B, C and D rings, and the compound (II) is a compound of formula (IIB):

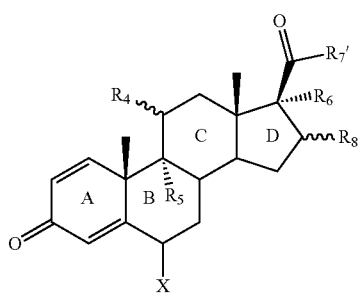

(IIB)

where $R_4$ and $R_5$, $R_6$, $R_7'$, $R_8$, ⁓⁓⁓ and ═══ are as defined in the compound (IB), where the oxo group located on the 20 carbon of the steroidal backbone can be in the free or protected form, where X is a halogen atom, preferably bromine or iodine, preferably bromine.

According to one embodiment of the processes according to the invention, the compound (I) is a compound of formula (IC):

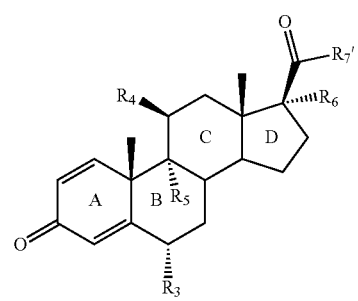

(IC)

where $R_3$ is an alkyl group comprising from 1 to 4 carbon atoms, preferably a methyl,
$R_4$ is either hydrogen or a hydroxyl group, in the free or protected form, for example a hydroxyl group in the esterified form, preferably in the acetylated form or in the trifluoroacetylated form,
$R_5$ is either hydrogen or a halogen atom, preferably fluorine,
$R_6$ is either hydrogen or a hydroxyl group, in the free or protected form, for example in the esterified form,
$R_7'$ is either hydrogen, or an alkyl group comprising from 1 to 3 carbon atoms, or a hydroxyl group, in the free or protected form, or a hydroxyalkyl group comprising from 1 to 3 carbon atoms, in the free or protected form, preferably a hydroxymethyl group, in the free or protected form, preferably a hydroxymethyl group in the acetylated form or in the trifluoroacetylated form,
and the compound (II) is a compound of formula (IIC):

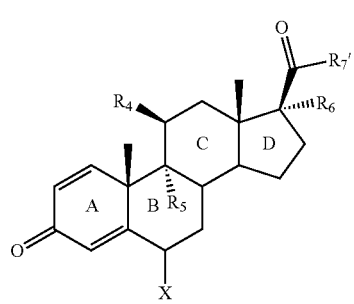

(IIC)

where $R_4$ and $R_5$, $R_6$ and $R_7'$ are as defined in the compound (IC),
where X is a halogen atom, preferably bromine or iodine, preferably bromine.

According to one embodiment of the processes according to the invention, in the compounds (IC) and (IIC), $R_7'$ is a methyl group or a hydroxymethyl group, in the free or protected form, preferably in the acetylated form or in the trifluoroacetylated form.

According to one embodiment of the processes according to the invention, in the compounds (IC) and (IIC), $R_6$ is a hydroxyl group, in the free or protected form.

According to one embodiment of the processes according to the invention, in the compounds (IC) and (IIC), $R_4$ and $R_7'$ are respectively hydroxyl and hydroxymethyl groups in the protected form, preferably in the esterified form, preferably in the acetylated form or in the trifluoroacetylated form.

According to one embodiment of the processes according to the invention, in the compounds (IC) and (IIC), $R_5$ is a hydrogen or fluorine atom.

Another subject matter of the present invention is compounds of formula (IIC):

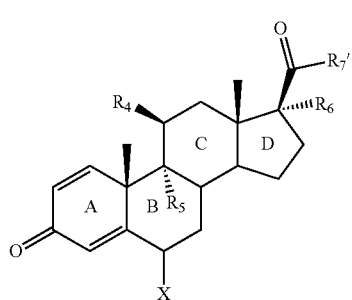

(IIC)

in which:
X is a halogen atom, preferably bromine,
$R_5$ is a hydrogen or fluorine atom,
$R_4$ and $R_7'$ are respectively hydroxyl and hydroxymethyl groups in the protected form, preferably in the esterified form, preferably in the acetylated form or in the trifluoroacetylated form,
$R_6$ is a hydroxyl group, in the free or protected form.

Another subject matter of the present invention is compounds corresponding to the formula (IIC) above, in which:
X is a halogen atom, preferably iodine or bromine, preferably bromine,
$R_5$ is a hydrogen atom,
$R_4$ and $R_7'$ are respectively hydroxyl and hydroxymethyl groups in the acetylated form or in the trifluoroacetylated form,
$R_6$ is a hydroxyl group, in the free or protected form, preferably in the free form.

Another subject matter of the present invention is processes as described above where the compound (I) is a compound of formula (ID):

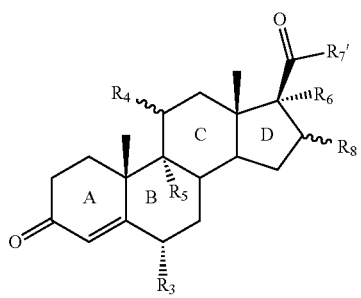

(ID)

where $R_3$ is an alkyl group comprising from 1 to 4 carbon atoms, preferably a methyl,
$R_4$ is either hydrogen, or a β-hydroxyl group, in the free or protected form, or an oxo group, in the free or protected form, $R_5$ is either hydrogen or a halogen atom, preferably fluorine,
$R_6$ is either hydrogen or a hydroxyl group, in the free or protected form,
$R_7'$ is either hydrogen, or an alkyl group comprising from 1 to 3 carbon atoms, or a hydroxyl group, in the free or protected form, or a hydroxyalkyl group comprising from 1 to 3 carbon atoms, in the free or protected form, preferably a hydroxymethyl group, in the free or protected form,
$R_8$ is either hydrogen or an α-alkyl group comprising from 1 to 3 carbon atoms, preferably a methyl group,
where the oxo group located on the 20 carbon of the steroidal backbone can be in the free or protected form,
where ~~~ represents either a single bond in the α or β position or in the plane of the A, B, C and D rings or, when this is possible, a double bond in the plane of the A, B, C and D rings, and where the compound (II) is a compound of formula (IID):

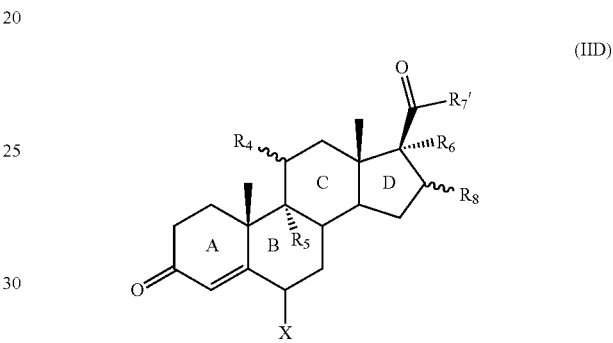

(IID)

where $R_4$ and $R_5$, $R_6$, $R_7'$, $R_8$ and ~~~ are as defined in the compound (ID),
where the oxo group located on the 20 carbon of the steroidal backbone can be in the free or protected form, in the same way as it is present in the compound (ID),
where X is a halogen atom, preferably bromine or iodine, preferably bromine.

According to one embodiment of such processes, in the compounds (ID) and (IID), $R_4$ is either a β-hydroxyl group, in the free or protected form, or an oxo group, in the free or protected form.

According to one embodiment of such processes, in the compounds (ID) and (IID), $R_7'$ is a methyl group or a hydroxymethyl group, in the free or protected form.

According to one embodiment of such processes, in the compounds (ID) and (IID), $R_6$ is a hydroxyl group, in the free or protected form.

According to one embodiment of such processes, in the compounds (ID) and (IID), $R_5$ is a hydrogen atom.

According to one embodiment of such processes, in the compounds (ID) and (IID), $R_7'$ is a hydroxymethyl group, in the free or protected form.

According to one embodiment of such processes, in the compounds (ID) and (IID), $R_8$ is an α-methyl group.

In one embodiment of such processes, in the compounds (ID) and (IID), $R_6$ is a hydroxyl group and $R_7'$ is a hydroxymethyl group, and $R_6$, $R_7'$ and the oxo group of the 20 carbon of the steroidal backbone are jointly protected in the form of an oxaspirane group.

According to one embodiment of such processes, the compounds (Id') and (IId') respectively have the formulae:

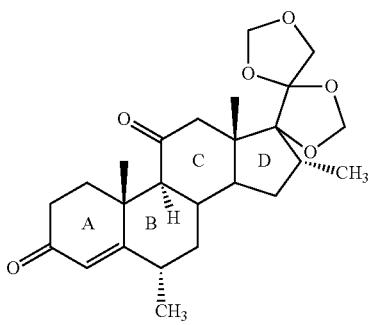

(Id')

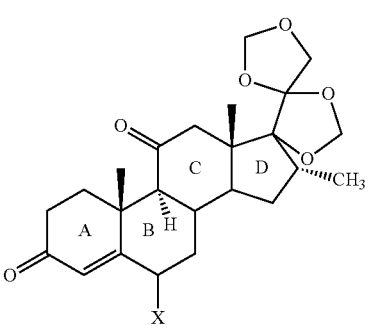

where X is a halogen atom, preferably bromine or iodine, preferably bromine.

Another subject matter of the present invention is compounds corresponding to the formula (IId) below:

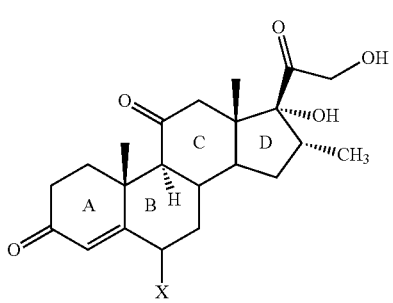

(IId)

where X is a halogen atom, preferably bromine or iodine, preferably bromine.

Another subject matter of the present invention is compounds corresponding to the formula (IId') below:

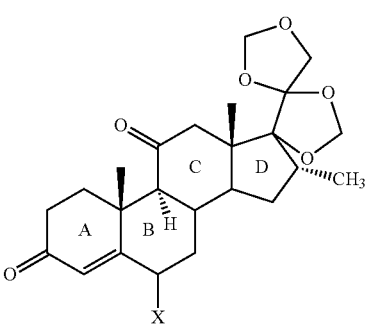

(IId')

where X is a halogen atom, preferably bromine or iodine, preferably bromine.

EXAMPLES

Example 1: (4αS,8R)-8-bromo-4α-methyl-5,6,7,8-tetrahydronaphth-2(4αH)-one 1 g (6.17 mmol) of (S)-4α-methyl-5,6,7,8-tetrahydronaphth-2(4αH)-one was charged to 60 ml of tetrachloromethane in a round-bottomed flask equipped with a magnetic stirrer. 1.65 g (9.25 mmol) of N-bromosuccinimide and 0.30 g (1.23 mmol) of benzoyl peroxide were then added. The resulting suspension was stirred under reflux for one hour. The resulting orange-colored solution was subsequently cooled to ambient temperature and 100 ml of dichloromethane were added. The reaction mixture was subsequently washed with a saturated aqueous sodium bicarbonate solution. The organic phases were subsequently washed with water, dried with sodium sulfate and filtered, and the solvent was evaporated; the product was subsequently purified on a chromatography column on silica gel in order to obtain the (4αS,8R)-8-bromo-4α-methyl-5,6,7,8-tetrahydronaphth-2(4αH)-one (0.6 g, 99% purity).

$^1$H NMR (CDCl$_3$, 400 MHz): δ (ppm), 6.73 (d, J=9.94 Hz, 1H), 6.27 (d, J=1.95 Hz, 1H), 6.20 (dd, J=9.94 and 1.75 Hz, 1H), 5.07-5.01 (m, 1H), 2.35 (ddd, J=15.01, 3.02 and 2.83 Hz, 1H), 2.30-2.17 (m, 1H), 2.02-1.92 (m, 1H), 1.92-1.71 (m, 2H), 1.62 (s, 3H), 1.41 (td, J=13.45 and 4.09 Hz, 1H).

$^{13}$C NMR (CDCl$_3$, 100 MHz): δ (ppm), 186.44, 160.67, 158.08, 127.02, 125.62, 50.97, 40.42, 36.44, 36.05, 27.74, 16.51.

Example 2: (4αS,8R)-4α,8-dimethyl-5,6,7,8-tetrahydronaphth-2(4αH)-one 104 mg of copper iodide were charged to dry tetrahydrofuran (3 ml) in a 10 ml dried Schlenk flask purged under argon and equipped with a magnetic stirrer and with a septum, and the gray mixture was cooled to 0° C. 1.09 mmol of MeLi were subsequently added dropwise, still at 0° C., and the yellow mixture was stirred at this temperature until a colorless solution was obtained. The lithium dimethylcuprate is thus formed in situ. The solution was cooled to −40° C. and a solution of 110 mg (0.45 mmol) of (4αS,8R)-8-bromo-4α-methyl-5,6,7,8-tetrahydronaphth-2(4αH)-one in dry tetrahydrofuran was added dropwise. After stirring at −40° C., 1.36 mmol of methyl iodide are added and the orange mixture is stirred for a further 30 minutes at this temperature; the reaction is subsequently halted with a 25% aqueous ammonium chloride solution and the reaction products are extracted with ethyl acetate; the organic phases are subsequently washed with aqueous sodium chloride solution, dried with sodium sulfate, filtered and concentrated under vacuum. The residue is subsequently purified on a chromatography column on silica gel in order to obtain the (4αS,8R)-4α,8-dimethyl-5,6,7,8-tetrahydronaphth-2(4αH)-one (27 mg, 98% purity).

Example 3: (4αS,8R)-4α,8-dimethyl-5,6,7,8-tetrahydronaphth-2(4αH)-one 104 mg of copper iodide were charged to dry tetrahydrofuran (3 ml) in a 10 ml dried Schlenk flask purged under argon and equipped with a magnetic stirrer and with a septum, and the gray mixture was cooled to 0° C. 1.09 mmol of MeLi were subsequently added dropwise, still at 0° C., and the yellow mixture was stirred at this temperature until a colorless solution was obtained. The lithium dimethylcuprate is thus formed in situ. The solution was cooled to −40° C. and a solution of 110 mg (0.45 mmol) of (4αS,8R)-8-bromo-4α-methyl-5,6,7,8-tetrahydronaphth-2(4αH)-one in dry tetrahydrofuran was added dropwise. After stirring at −40° C. for 10 minutes, the reaction is subsequently halted with a 25% aqueous ammonium chloride solution and the reaction products are extracted with ethyl acetate; the organic phases are subsequently washed with aqueous sodium chloride solution, dried with sodium sulfate, filtered and concentrated under vacuum. The residue is subsequently purified on a chromatography column on silica gel in order to obtain the (4αS,8R)-4α,8-dimethyl-5,6,7,8-tetrahydronaphth-2(4αH)-one (28 mg, 98% purity).

Example 4: (4αS,8R)-4α,8-dimethyl-5,6,7,8-tetrahydronaphth-2(4αH)-one 104 mg of copper iodide were charged to dry tetrahydrofuran (3 ml) in a 10 ml dried Schlenk flask purged under argon and equipped with a magnetic stirrer and with a septum, and the gray mixture was cooled to 0° C. 0.55 mmol of MeLi were subsequently added dropwise, still at 0° C., and the yellow mixture was stirred at this temperature until a colorless solution was obtained. The lithium monomethylcuprate is thus formed in situ. The solution was cooled to −40° C. and a solution of 110 mg (0.45 mmol) of (4αS,8R)-8-bromo-4α-methyl-5,6,7,8-tetrahydronaphth-2(4αH)-one in dry tetrahydrofuran was added dropwise. After stirring at −40° C. for 10 minutes, the reaction is subsequently halted with a 25% aqueous ammonium chloride solution and the reaction products are extracted with ethyl acetate; the organic phases are subsequently washed with aqueous sodium chloride solution, dried with sodium sulfate, filtered and concentrated under vacuum. The residue is subsequently purified on a chromatography column on silica gel in order to obtain the (4αS,8R)-4α,8-dimethyl-5,6,7,8-tetrahydronaphth-2(4αH)-one (36 mg, 98% purity).

$^1$H NMR (CDCl$_3$, 300 MHz): δ (ppm), 6.78 (d, J=9.95 Hz, 1H), 6.21 (dd, J=9.81 and 1.80 Hz, 1H), 6.11 (t, J=1.66 Hz, 1H), 2.58-2.43 (m, 1H), 2.04-1.93 (m, 1H), 1.89-1.63 (m, 3H), 1.36-1.28 (m, 1H), 1.25 (s, 3H), 1.13 (d, J=6.63 Hz, 3H), 1.03 (dd, J=12.72 and 4.42 Hz, 1H).

$^{13}$C NMR (CDCl$_3$, 75 MHz): δ (ppm), 187.41, 171.09, 158.08, 126.28, 121.41, 41.20, 38.55, 36.96, 34.09, 23.35, 20.98, 17.63.

Example 5: Diacetylation of Prednisolone, in Order to Protect the Hydroxyls in the 11 and 21 Positions

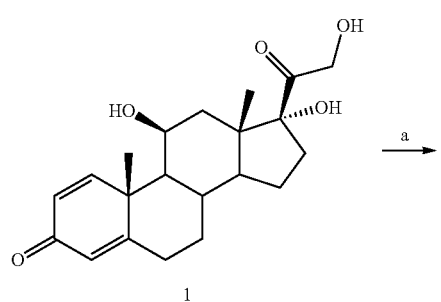

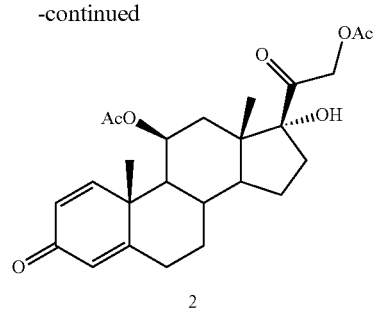

Prednisolone (21.60 g, 60 mmol) is introduced into and dissolved in dichloromethane (300 ml) in a 500 ml round-bottomed flask. DMAP (1.5 g, 12 mmol, 0.2 equiv.), triethylamine (24.2 ml, 180 mmol, 3 equiv.) and acetic anhydride (17.0 ml, 180 mmol, 3.0 equiv.) are successively added to the reaction medium and then the latter is stirred at 25° C. The progress of the reaction is monitored by HPLC. After stirring for 17 h, the conversion of the prednisolone is complete. The reaction medium is quenched with a saturated ammonium chloride solution and then the aqueous phase is extracted with dichloromethane. The organic phase is dried over magnesium sulfate and then concentrated under reduced pressure. The crude product is purified by chromatography on silica gel (dichloromethane/methanol 99:1) to give the compound 2 with a yield of 90% (purity 98%).

Example 6: Bromination at the 6 Position of Prednisolone Diacetate

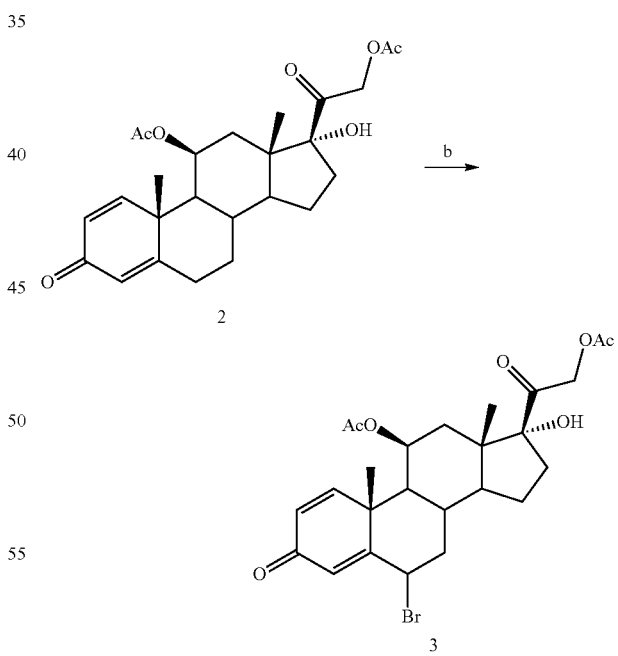

NBS (3.56 g, 20 mmol, 2.0 equiv.) and benzoyl peroxide (0.48 g, 2 mmol, 0.2 equiv.) are added to a solution of diacetylated prednisolone 2 (4.44 g, 10 mmol) in carbon tetrachloride (500 ml). The reaction medium is brought to reflux and stirred for approximately 3 h. The progress of the reaction is monitored by HPLC. After 3 h, the reaction mixture no longer changes. The reaction medium is cooled to ambient temperature and then filtered. The round-bottomed flask is rinsed 3 times with carbon tetrachloride.

The filtrate is subsequently concentrated under vacuum. The crude product is extracted with dichloromethane and washed with a 10% sodium hydrogencarbonate solution. The organic phase is dried over magnesium sulfate and then concentrated under reduced pressure. The crude product is purified by chromatography on silica gel (dichloromethane/methanol 99:1) to give the compound 3 with a yield of 84% (purity 93%).

It should be noted that it is also possible to use chlorobenzene as solvent for this synthesis.

Example 7: 6α-Methylprednisolone Diacetate 228 mg of copper iodide were charged to dry tetrahydrofuran (6 ml) in a 10 ml dried Schlenk flask purged under argon and equipped with a magnetic stirrer and with a septum, and the gray mixture was cooled to 0° C. 2.4 mmol of MeLi were subsequently added dropwise, still at 0° C., and the yellow mixture was stirred at this temperature until a colorless solution was obtained. The lithium dimethylcuprate is thus formed in situ. The solution was cooled to −40° C. and a solution of 523 mg (1.0 mmol) of 6β-bromoprednisolone diacetate in dry tetrahydrofuran (2 ml) was added dropwise.

After stirring at −40° C. for 10 minutes, the reaction is subsequently halted with a 25% aqueous ammonium chloride solution and the reaction products are extracted with ethyl acetate; the organic phases are subsequently washed with aqueous sodium chloride solution, dried with sodium sulfate, filtered and concentrated under vacuum. The residue is subsequently purified on a chromatography column on silica gel in order to obtain the 6α-methylprednisolone diacetate (120 mg, purity 85%).

Example 8: 6α-Methylprednisolone Diacetate 228 mg (1.2 mmol) of copper iodide were charged to dry tetrahydrofuran (6 ml) in a 10 ml dried Schlenk flask purged under argon and equipped with a magnetic stirrer and with a septum, and the gray mixture was cooled to 0° C. 1.2 mmol of MeLi were subsequently added dropwise, still at 0° C., and the yellow mixture was stirred at this temperature until an orange suspension was obtained. The monomethylcuprate is thus formed in situ. The solution was cooled to −40° C. and a solution of 523 mg (1.0 mmol) of 6β-bromoprednisolone diacetate in dry tetrahydrofuran (2 ml) was added dropwise.

After stirring at −40° C. for 10 minutes, the reaction is subsequently halted with a 25% aqueous ammonium chloride solution and the reaction products are extracted with ethyl acetate; the organic phases are subsequently washed with aqueous sodium chloride solution, dried with sodium sulfate, filtered and concentrated under vacuum. The residue is subsequently purified on a chromatography column on silica gel in order to obtain the 6α-methylprednisolone diacetate (160 mg, purity 98%).

$^1$H NMR (CDCl$_3$, 600 MHz): δ (ppm), 6.96 (d, J=9.98 Hz, 1H), 6.27 (dd, J=9.98 and 1.76 Hz, 1H), 6.03 (d, J=1.76 Hz, 1H), 5.54 (d, J=2.93 Hz, 1H), 5.09 (d, J=17.02 Hz, 1H), 4.68 (d, J=17.61 Hz, 1H), 2.79-2.73 (m, 1H), 2.64-2.57 (m, 1H), 2.21 (qd, J=11.25 and 4.40 Hz, 1H), 2.15 (s, 3H), 2.09 (s, 3H), 2.06-2.01 (m, 2H), 1.85-1.80 (m, 2H), 1.77-1.71 (m, 1H), 1.54-1.41 (m, 2H), 1.27 (s, 3H), 1.21-1.15 (m, 1H), 1.13 (d, J=6.46 Hz, 3H), 0.94-0.85 (m, 2H), 0.84 (s, 3H).

$^{13}$C NMR (CDCl$_3$, 150 MHz): δ (ppm), 204.64, 186.05, 171.99, 170.30, 169.66, 155.19, 127.67, 119.74, 89.07, 71.12, 67.45, 54.04, 50.81, 47.18, 43.06, 42.30, 35.24, 34.37, 32.86, 31.39, 23.50, 21.57, 20.90, 20.27, 17.47, 16.36.

The invention claimed is:

1. A process for the preparation of a compound of formula (I):

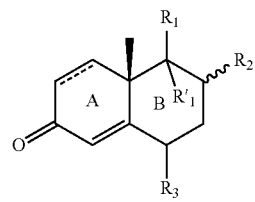

wherein for the compound of formula (I):
R$_1$ and R$_2$ together form C and D rings of a steroidal carbon-based backbone, wherein said C and D rings optionally comprise one or more double bonds and are optionally substituted by one or more moieties selected from the group consisting of:
linear or branched alkyl groups comprising from 1 to 12 carbon atoms,
acyl groups comprising from 1 to 12 carbon atoms and optionally substituted by one or more hydroxyl groups,
carboxyl, hydroxyl or oxo groups, and
halogen atoms,
wherein the acyl, carboxyl, hydroxyl, and oxo groups are in free or protected form, and wherein each position of said C and D rings is optionally substituted with one or, where possible, two said moieties;
R'$_1$ is a hydrogen or halogen atom, and R$_1$ and R'$_1$ are located on either side of the plane of the A and B rings;
R$_3$ is an alkyl group comprising from 1 to 4 carbon atoms;

-------- is a single bond or a double bond; and

∿∿∿ is a single bond in the α or β position of the A and B rings, or a double bond in the plane of the A and B rings, wherein said process comprises alkylation of a compound of formula (II):

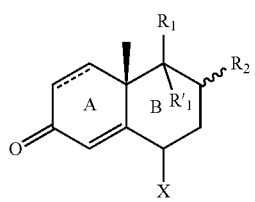

wherein for the compound of formula (II), R$_1$, R'$_1$, R$_2$,

-------- and ∿∿∿ are as defined for the compound of formula (I), and X is a halogen atom;
with an organometallic alkylating agent, optionally in the presence of a metal catalyst, wherein the group R$_3$, present in the organometallic alkylating agent, replaces group X of the compound of formula (II), to obtain the compound of formula (I).

2. The process according to claim 1, wherein the organometallic alkylating agent is selected from the group consisting of organolithium compounds of formula $R_3Li$, organomagnesium compounds of formula $R_3MgX'$, organozinc compounds of formula $R_3ZnX'$, where X' is a halogen atom, organocopper compounds of formula $R_3Cu$, lithium organocuprates of formula $(R_3)_2CuLi$, organocyanocuprates of formula $R_3CuCNLi$ or $(R_3)_2CuCN(Li)_2$, halocuprates of formula $R_3CuLiX''$, where X" is a halogen atom, organoboron compounds of formula $R_3B(OH)_2$ and organotrifluoroborates of formula $R_3BF_3K$.

3. The process according to claim 2, wherein the organometallic alkylating agent is selected from the group consisting of organomagnesium compounds of formula $R_3MgX'$, where X' is a halogen atom, organocopper compounds of formula $R_3Cu$, lithium organocuprates of formula $(R_3)_2CuLi$, organocyanocuprates of formula $R_3CuCNLi$ or $(R_3)_2CuCN(Li)_2$, and halocuprates of formula $R_3CuLiX''$, where X" is a halogen atom.

4. The process according to claim 3, wherein the organometallic alkylating agent is an organomagnesium compound of formula $R_3MgX'$, where X' is a halogen atom, and wherein the alkylation is carried out in the presence of a copper catalyst.

5. The process according to claim 3, wherein the organometallic alkylating agent is a halocuprate of formula $R_3CuLiX''$, where X" is a halogen atom.

6. The process according to claim 3, wherein the organometallic alkylating agent is a lithium organocuprate of formula $(R_3)_2CuLi$ or an organocyanocuprate of formula $(R_3)_2CuCN(Li)_2$.

7. The process according to claim 3, wherein the organometallic alkylating agent is a lithium organocuprate of formula $(R_3)_2CuLi$, and
wherein the alkylation comprises reaction of the compound of formula (II) with said lithium organocuprate, followed by reaction of the resulting compound with a second alkylating agent of formula $R_3X'''$, where X''' is a halogen atom.

8. The process according to claim 1, wherein the compound of formula (II) is obtained by halogenation of a compound of formula (III):

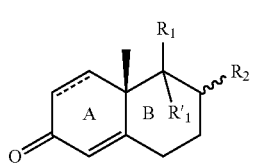

wherein for the compound of formula (III), $R_1$, $R'_1$, $R_2$,
-------- and ∼∼∼∼ are as defined in claim 1.

9. The process according to claim 1, wherein X is a bromine atom.

10. The process according to claim 9, wherein the compound of formula (II) is obtained by reaction of the compound of formula (III) with an N-bromoimide in the presence of a radical initiator.

11. The process according to claim 1, wherein the compound of formula (I) is a steroidal compound of formula (IA):

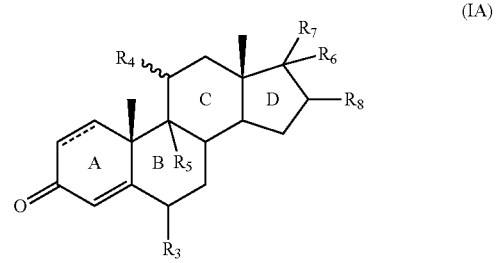

wherein for the compound of formula (IA):
$R_3$ is an alkyl group comprising from 1 to 4 carbon atoms;
$R_4$ is hydrogen, or a hydroxyl or oxo group, wherein the hydroxyl or oxo group is in free or protected form;
$R_5$ is hydrogen or a halogen atom;
$R_6$ is hydrogen or a hydroxyl group, in free or protected form;
$R_7$ is hydrogen or a —C(O)$R_7'$ or —C(OR)$_2R_7'$ group, where R is a protective group for the carbonyl functional group and where $R_7'$ is selected from the group consisting of hydrogen, an alkyl group comprising from 1 to 3 carbon atoms, a hydroxyl group, in free or protected form, and a hydroxyalkyl group comprising from 1 to 3 carbon atoms, in free or protected form, or
$R_6$ and $R_7$ together form an oxo group in the 17 position of the steroidal backbone of the compound of formula (IA);
$R_8$ is hydrogen or an alkyl group comprising from 1 to 3 carbon atoms;
wherein the $R_6$ and $R_7$ groups are located on either side of the plane of the A, B, C and D rings;
-------- is a single bond or a double bond;
∼∼∼∼ is a single bond in the α or β position or in the plane of the A, B, C and D rings or, where possible, a double bond in the plane of the A, B, C and D rings; and
wherein the compound of formula (II) is a compound of formula (IIA):

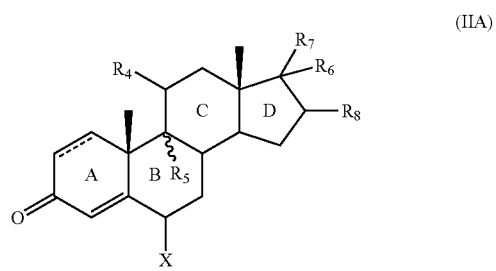

wherein for the compound of formula (IIA), $R_4$, $R_5$, $R_6$, $R_7$, $R_8$, -------- and ∼∼∼∼ are as defined for the compound of formula (IA), and X is a halogen atom.

12. The process according to claim 11, wherein the compound of formula (I) is a steroidal compound of formula (IA):

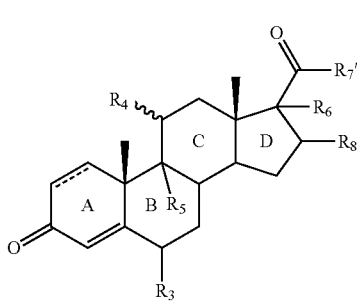

(IA)

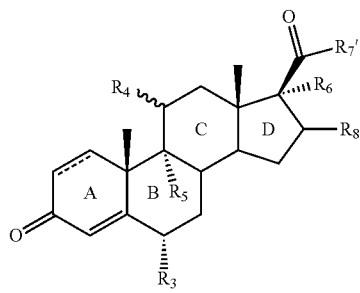

(IB)

wherein for the compound of formula (IA):
  R$_3$ is an alkyl group comprising from 1 to 4 carbon atoms;
  R$_4$ is hydrogen, or a hydroxyl or oxo group, wherein the hydroxyl or oxo group is in free or protected form;
  R$_5$ is hydrogen or a halogen atom;
  R$_6$ is hydrogen, or a hydroxyl group, in free or protected form;
  R$_7$' is selected from the group consisting of hydrogen, an alkyl group comprising from 1 to 3 carbon atoms, a hydroxyl group, in free or protected form, and a hydroxyalkyl group comprising from 1 to 3 carbon atoms, in free or protected form;
  R$_8$ is hydrogen or an alkyl group comprising from 1 to 3 carbon atoms;
  wherein the R$_6$ and —C(O)R$_7$' groups are located on either side of the plane of the A, B, C and D rings;
  the oxo group located on the carbon in the 20 position of the steroidal backbone is in free or protected form;
  -------- is a single bond or a double bond;
  ∿∿∿∿ is a single bond in the α or β position or in the plane of the A, B, C and D rings or, where possible, a double bond in the plane of the A, B, C and D rings; and
wherein the compound of formula (II) is a compound of formula (IIA):

wherein for the compound of formula (IB):
  R$_3$ is an alkyl group comprising from 1 to 4 carbon atoms;
  R$_4$ is selected from the group consisting of hydrogen, a β-hydroxyl group, in free or protected form, and an oxo group, in free or protected form;
  R$_5$ is hydrogen or a halogen atom;
  R$_6$ is hydrogen, or a hydroxyl group, in free or protected form;
  R$_7$' is selected from the group consisting of hydrogen, an alkyl group comprising from 1 to 3 carbon atoms, a hydroxyl group, in free or protected form, and a hydroxyalkyl group comprising from 1 to 3 carbon atoms, in free or protected form;
  R$_8$ is hydrogen or an α-alkyl group comprising from 1 to 3 carbon atoms;
  the oxo group located on the 20 carbon of the steroidal backbone is in free or protected form;
  -------- is a single bond or a double bond;
  ∿∿∿∿ is a single bond in the α or β position or in the plane of the A, B, C and D rings or, where possible, a double bond in the plane of the A, B, C and D rings; and
wherein the compound of formula (II) is a compound of formula (IIB):

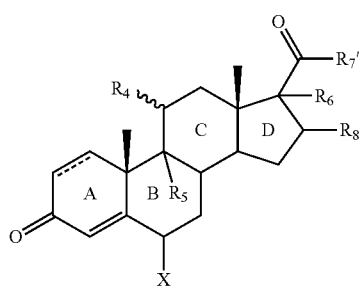

(IIA)

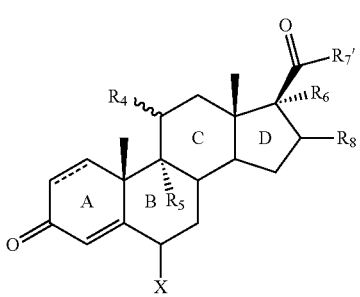

(IIB)

wherein for the compound of formula (IIA):
  R$_4$, R$_5$, R$_6$, R$_7$', R$_8$, -------- and ∿∿∿∿ are as defined for the compound of formula (IA);
  the oxo group located on the 20 carbon of the steroidal backbone is in free or protected form; and
  X is a halogen atom.
13. The process according to claim 12, wherein the compound of formula (I) is a compound of formula (IB):

wherein for the compound of formula (IIB):
  R$_4$, R$_5$, R$_6$, R$_7$', R$_8$, -------- and ∿∿∿∿ are as defined for the compound of formula (IB);
  the oxo group located on the 20 carbon of the steroidal backbone is in free or protected form; and
  X is a halogen atom.
14. The process according to claim 13, wherein the compound of formula (I) is a compound of formula (IC):

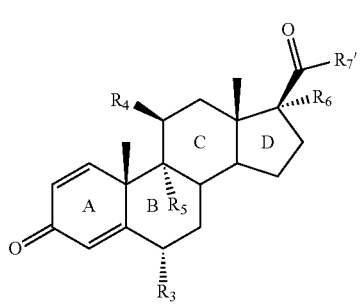

(IC)

wherein for the compound of formula (IC):
- $R_3$ is an alkyl group comprising from 1 to 4 carbon atoms;
- $R_4$ is hydrogen, or a hydroxyl group, in free or protected form;
- $R_5$ is hydrogen or a halogen atom;
- $R_6$ is hydrogen, or a hydroxyl group, in free or protected form;
- $R_7'$ is selected from the group consisting of hydrogen, an alkyl group comprising from 1 to 3 carbon atoms, a hydroxyl group, in free or protected form, and a hydroxyalkyl group comprising from 1 to 3 carbon atoms, in free or protected form; and wherein the compound of formula (II) is a compound of formula (IIC):

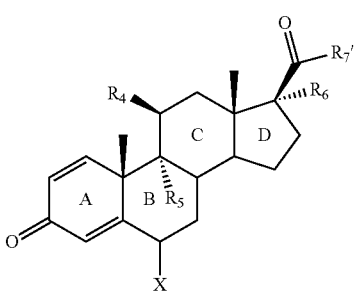

(IIC)

wherein for the compound of formula (IIC), $R_4$, $R_5$, $R_6$ and $R_7'$ are as defined for the compound of formula (IC), and X is a halogen atom.

15. The process according to claim 14, wherein for the compounds of formulae (IC) and (IIC), $R_7'$ is a methyl group or a hydroxymethyl group, in free or protected form.

16. The process according to claim 14, wherein for the compounds of formulae (IC) and (IIC), $R_6$ is a hydroxyl group, in free or protected form.

17. The process according to claim 14, wherein for the compounds of formulae (IC) and (IIC), $R_4$ is a hydroxyl group in protected form and $R_7'$ is a hydroxymethyl group in protected form.

18. The process according to claim 14, wherein for the compounds of formulae (IC) and (TIC), $R_5$ is a hydrogen or fluorine atom.

19. The process according to claim 12, wherein the compound of formula (I) is a compound of formula (ID):

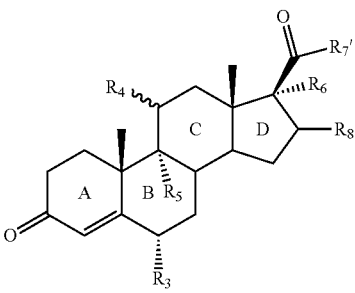

(ID)

wherein for the compound of formula (ID):
- $R_3$ is an alkyl group comprising from 1 to 4 carbon atoms;
- $R_4$ is selected from the group consisting of hydrogen, a β-hydroxyl group, in free or protected form, and an oxo group, in free or protected form;
- $R_5$ is hydrogen or a halogen atom;
- $R_6$ is hydrogen, or a hydroxyl group, in free or protected form;
- $R_7'$ is selected from the group consisting of hydrogen, an alkyl group comprising from 1 to 3 carbon atoms, a hydroxyl group, in free or protected form, and a hydroxyalkyl group comprising from 1 to 3 carbon atoms, in free or protected form;
- $R_8$ is hydrogen or an α-alkyl group comprising from 1 to 3 carbon atoms;
- the oxo group located on the 20 carbon of the steroidal backbone is in free or protected form;
- ⁓ is a single bond in the α or β position or in the plane of the A, B, C and D rings or, where possible, a double bond in the plane of the A, B, C and D rings; and wherein the compound of formula (II) is a compound of formula (IID):

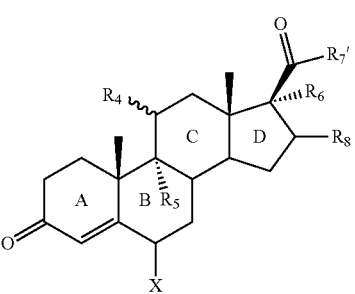

(IID)

wherein for the compound of formula (IID):
- $R_4$, $R_5$, $R_6$, $R_7'$, $R_8$ and ⁓ are as defined for the compound of formula (ID);
- the oxo group located on the 20 carbon of the steroidal backbone is in free or protected form, in the same way as it is present in the compound of formula (ID); and
- X is a halogen atom.

20. The process according to claim 19, wherein for the compounds of formulae (ID) and (IID), $R_4$ is a β-hydroxyl group, in free or protected form, or an oxo group, in free or protected form.

21. The process according to claim 19, wherein for the compounds of formulae (ID) and (IID), $R_7'$ is a methyl group or a hydroxymethyl group, in free or protected form.

22. The process according to claim 19, wherein for the compounds of formulae (ID) and (IID), $R_6$ is a hydroxyl group, in free or protected form.

23. The process according to claim 19, wherein for the compounds of formulae (ID) and (IID), $R_5$ is a hydrogen atom.

24. The process according to claim 19, wherein for the compounds of formulae (ID) and (IID), $R_7'$ is a hydroxymethyl group, in free or protected form.

25. The process according to claim 19, wherein for the compounds of formulae (ID) and (IID), $R_8$ is an α-methyl group.

26. The process according to claim 19, wherein for the compounds of formulae (ID) and (IID), $R_6$ is a hydroxyl group, $R_7'$ is a hydroxymethyl group, and $R_6$, $R_7'$ and the oxo group of the 20 carbon of the steroidal backbone are jointly protected in the form of an oxaspirane group.

27. The process according to claim 26, wherein the compounds of formulae (ID) and (IID) are the compounds of formulae (Id') and (IId'), respectively:

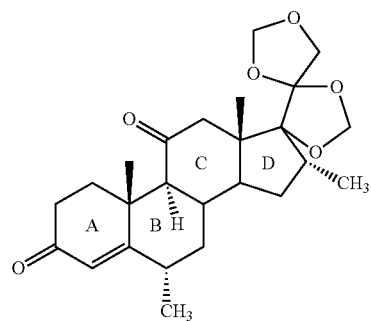
(Id')

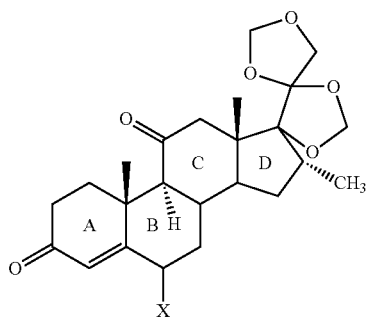
(IId')

wherein for the compound of formula (IId'), X is a halogen atom.

* * * * *

UNITED STATES PATENT AND TRADEMARK OFFICE
CERTIFICATE OF CORRECTION

PATENT NO.         : 9,783,569 B2
APPLICATION NO.    : 15/032251
DATED              : October 10, 2017
INVENTOR(S)        : Stéphanie Duez et al.

It is certified that error appears in the above-identified patent and that said Letters Patent is hereby corrected as shown below:

In the Claims

At Column 22, Claim number 11, Line number 25: please replace "functional group" with --functional group,--;

At Column 22, Claim number 11, Line number 47: please replace the chemical structure

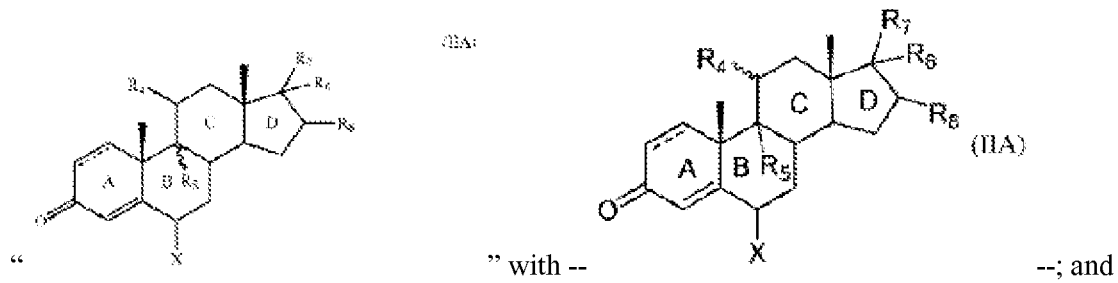

At Column 25, Claim number 18, Line number 63: please replace "(TIC)" with --(IIC)--.

Signed and Sealed this
Thirteenth Day of February, 2018

Andrei Iancu
*Director of the United States Patent and Trademark Office*